Figure 1:
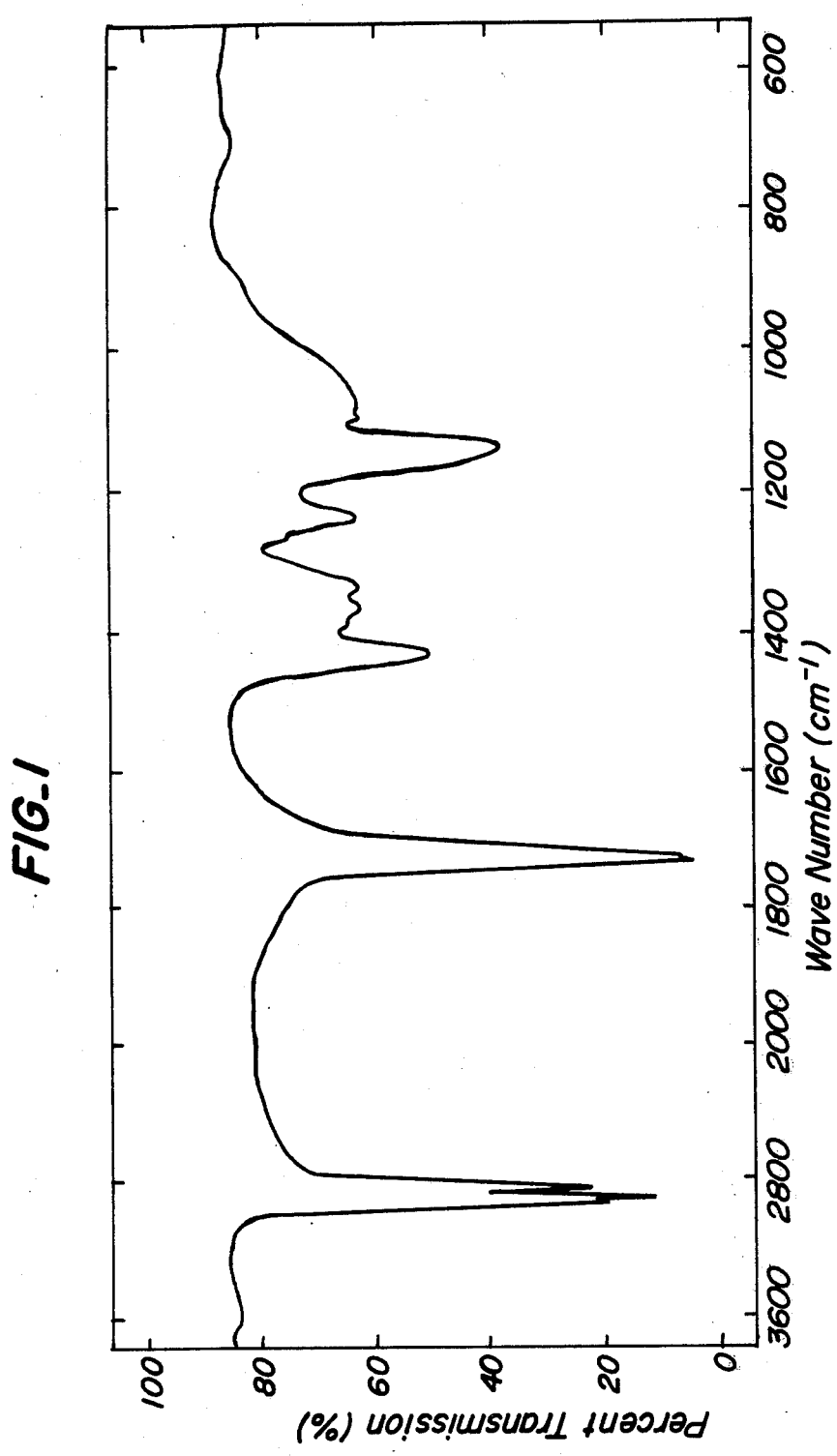

United States Patent [19]

Ishida et al.

[11] 4,128,483

[45] Dec. 5, 1978

[54] SULFUR-CONTAINING COMPLEX ESTERS AND SPIN FINISHING COMPOSITIONS USING SAID ESTERS

[75] Inventors: Shiro Ishida, Takarazuka; Genuemon Funatsuki, Amagasaki; Hiromi Izaiku, Nishinomiya; Jiro Hirano, Takatsuki, all of Japan

[73] Assignee: Nippon Oil and Fats Co. Ltd., Tokyo, Japan

[21] Appl. No.: 884,905

[22] Filed: Mar. 9, 1978

[30] Foreign Application Priority Data

Mar. 16, 1977 [JP] Japan .................................. 52-28085

[51] Int. Cl.$^2$ ........................................... D06M 13/26
[52] U.S. Cl. ..................... 252/8.6; 252/8.7; 560/154
[58] Field of Search .................. 252/8.6, 8.7; 560/154

[56] References Cited

U.S. PATENT DOCUMENTS

| 2,575,196 | 11/1951 | Smith ................................ 260/485 |
| 3,086,044 | 4/1963 | Kerschner et al. ................. 560/154 |
| 3,959,560 | 5/1976 | Sturwold et al. .................... 252/8.6 |

FOREIGN PATENT DOCUMENTS 52-103589  8/1977  Japan.

*Primary Examiner*—William E. Schulz
*Attorney, Agent, or Firm*—Stevens, Davis, Miller & Mosher

[57] ABSTRACT

Novel sulfur-containing complex esters are constituted with thiodipropionic acid, polyhydric alcohols having at least three valencies and monobasic acids having 5 – 24 carbon atoms. The sulfur-containing complex esters are excellent in the thermal stability and the lubricity, so that these esters are useful as base oils for spin finishing compositions for synthetic fibers.

5 Claims, 4 Drawing Figures

SULFUR-CONTAINING COMPLEX ESTERS AND SPIN FINISHING COMPOSITIONS USING SAID ESTERS

The present invention relates to novel sulfur-containing complex esters and to spin finishing compositions for synthetic fibers using said novel sulfur-containing complex esters as base oils.

The novel sulfur-containing complex esters of the present invention contains three ingredients of thiodipropionic acid, polyhydric alcohols and monobasic acids.

The polydric alcohols constituting the sulfur-containing complex esters of the present invention are alcohols having at least three valencies and include trimethylolpropane, trimethylolethane, glycerine, pentaerythritol, dipentaerythritol, sorbitol, etc.

The monobasic acids constituting the sulfur-containing complex esters of the present invention are the monobasic acids having 5-24 carbon atoms including fatty acids obtained from animal and vegetable fats and oils and synthetic fatty acids obtained by paraffin oxidation process, oxo synthesis process, Koch process and alkali fusion process, for example valeric acid, isovaleric acid, caproic acid, enanthic acid, caprylic acid, pelargonic acid, capric acid, undecanoic acid, lauric acid, tridecanoic acid, myristic acid, pentadecanoic acid, palmitic acid, margaric acid, stearic acid, nonadecanoic acid, arachidic acid, behenic acid, lignoceric acid, oleic acid, isostearic acid, 2-ethylhexanoic acid, neoheptanoic acid, neononanoic acid and the like, and the mixtures thereof, coconut oil fatty acids, tallow fatty acids and the like.

The molecular weight of the sulfur-containing complex esters of the present invention is determined by the molecular weight and the reaction molar ratio of thiodipropionic acid, the polyhydric alcohols and the monobasic acids and is preferred to be 700-3,000.

The sulfur-containing complex esters of the present invention are obtained by usual esterification reaction from thiodipropionic acid, the polyhydric alcohols and the monobasic acids. The esterification reaction is carried out by using catalysts for esterification under atmospheric pressure or a reduced pressure under an inert gas atmosphere, such as nitrogen gas, at a temperature of 70°-240° C. for 2-20 hours, preferably at a temperature of 100°-150° C. for 2-10 hours. In this case, the esterification reaction may be carried out by adding a solvent, such as toluene and xylene, which forms an azeotrope with water.

As the catalysts for the esterification reaction, mention may be made of catalysts used in the usual esterification reaction, such as sulfuric acid, phosphoric acid, phosphorous acid, hypophosphorous acid, perchloric acid, p-toluenesulfonic acid, benzenesulfonic acid, methanesulfonic acid, ethanesulfonic acid, dodecylbenzenesulfonic acid, zinc powder, tin powder, tin chloride, zinc oxide, calcium hydroxide and the like.

After the esterification reaction has been completed, unreacted or superfluous monobasic acids are distilled off under a reduced pressure of 0.1-40 mmHg. Then, the remaining monobasic acids and catalysts are neutralized by means of an aqueous alkali solution, such as sodium hydroxide, and then water washing is effected. If it is necessary to further effect bleaching, an adsorbent, such as active carbon or activated clay is used.

The sulfur-containing complex esters of the present invention contain thiodipropionic acid as one component and sulfur atom is contained in the ester chain as sulfide bonds, so that the sulfur-containing complex esters are high in the thermal stability. Furthermore, the sulfur-containing complex esters are excellent in the lubricity in view of a low friction coefficient, a high load carrying capacity and a high viscosity index, so that said complex esters are particularly useful as lubricants which are used at high temperatures. That is, the sulfur-containing complex esters of the present invention are useful as base oils or additives for hydraulic oils, rolling oils, cutting oils, greases, a textile treating compositions and the like.

When the sulfur-containing complex esters of the present invention are used as a rolling oil, said esters show good properties as a complex ester upon rolling and said esters are easily docomposed and volatilized upon annealing, so that said esters can be used as a rolling oil which does not need electrolytic cleaning process which is conducted for the purpose of removal of rolling oil. This is because the sulfide bonds are cut at the annealing step at about 700° C. and these esters are decomposed into low molecular weight ester and easily volatilized.

Compounds containing sulfide bonds are frequently used as extreme-pressure additives of lubricating oils but are low molecular weight, so that unpleasant odor is generated owing to the volatilization, sludge is formed, the extreme-pressure property is lowered with lapse of time and other undesirable phenomena occur. The sulfur-containing complex esters of the present invention are high molecular weight sulfide compounds, so that said complex esters have not such defects.

In addition, sulfur atoms together with the ester group strongly bond to the metal surface, so that the excellent extreme-pressure property is attained.

The textile treating compositions for synthetic fibers are usually prepared by compounding lubricating ingredients, surface active agents, antistatic agents and the like. As the lubricating ingredients, use may be made of mineral oils, animal and vegetable fats and oils, synthetic esters and the like, but problems of smoke generation, coloring, formation of tar and polymerization occur in the production steps of melt spinning, drawing, false twisting and the other processing steps of synthetic fibers. Thus, the thermal stability is required in the lubricating ingredients.

When the sulfur-containing complex esters of the present invention are used as the lubricating ingredients, the chain reaction of the thermal decomposition is stopped by the free radical scavenging effect possessed by the sulfide bond, so that the smoke generation, coloring, formation of tar and polymerization are restrained. As mentioned above, the sulfur-containing complex esters of the present invention are excellent in the thermal stability, so that said complex esters are preferable as the base oils or additives of the textile treating compositions, particularly the spin finishing compositions for synthetic fibers.

The spin finishing compositions according to the present invention are prepared by compounding the sulfur-containing complex esters as the lubricating ingredients, surface active agents and a necessary amount of antistatic agents.

The spin finishing compositions according to the present invention contains 50-98% by weight of the sulfur-containing complex esters, 1-45% by weight of surface active agents and 0–5% by weight of antistatic agents, preferably 70–98% by weight of the sulfur-containing complex esters, 2–30% by weight of surface active agents and 0–5% by weight of antistatic agents. The compounding ratio is determined by the conditions for using the spin finishing compositions.

The surface active agents are ones usually used for the spin finishing compositions, for example polyoxyethylene lauryl ether, polyoxyethylene oleyl ether, polyoxyethylene nonylphenyl ether, polyoxyethylene castor oil, polyethyleneglycol dilaurate, glycerol monostearate, glycerol monooleate and the like. When the spin finishing compositions are used in the form of an aqueous emulsion, the surface active agents are preferably used as a mixture of two or more surface active agents for stabilization of the emulsion.

The antistatic agents are the surface active agents usually used for the spin finishing compositions, for example sodium lauryl phosphate, sodium oleyl phosphate, potassium polyoxyethylene lauryl ether phosphate, potassium cetyl sulfate and the like.

Furthermore, the spin finishing compositions may use the sulfur-containing complex esters together with lubricating ingredients usually used for the spin finishing compositions. In this case, it is necessary that at least 10% by weight, preferably at least 30% by weight of the total lubricating ingredients are the sulfur-containing complex esters.

As the lubricating ingredients generally used for the spin finishing compositions, mention may be made of mineral oils, animal and vegetable fats and oils and synthetic esters, for example spindle oil, soybean oil, rapeseed oil, butyl stearate, isopropyl myristate, 2-ethylhexyl stearate, trimethylolpropane tripelargonate, trimethylolpropane tricaprylate, trimethylolpropane, trilaurate, oleyl oleate and the like.

The spin finishing compositions according to the present invention are deposited in an amount of 0.1–2% by weight as oil content on synthetic fibrous filaments in the composition form or the form of an aqueous emulsion.

Synthetic fibers in which the spin finishing compositions according to the present invention are applicable, include polyamides, polyesters, polyacrylonitriles, polyolefins and the like and the fibers may be filaments and yarns.

The spin finishing compositions according to the present invention may be used in the melt spinning step of the synthetic fibers but other than said step, may be used in the drawing step, the false twisting step and the other processing steps.

The present invention will be explained in more detail.

Figure 2:
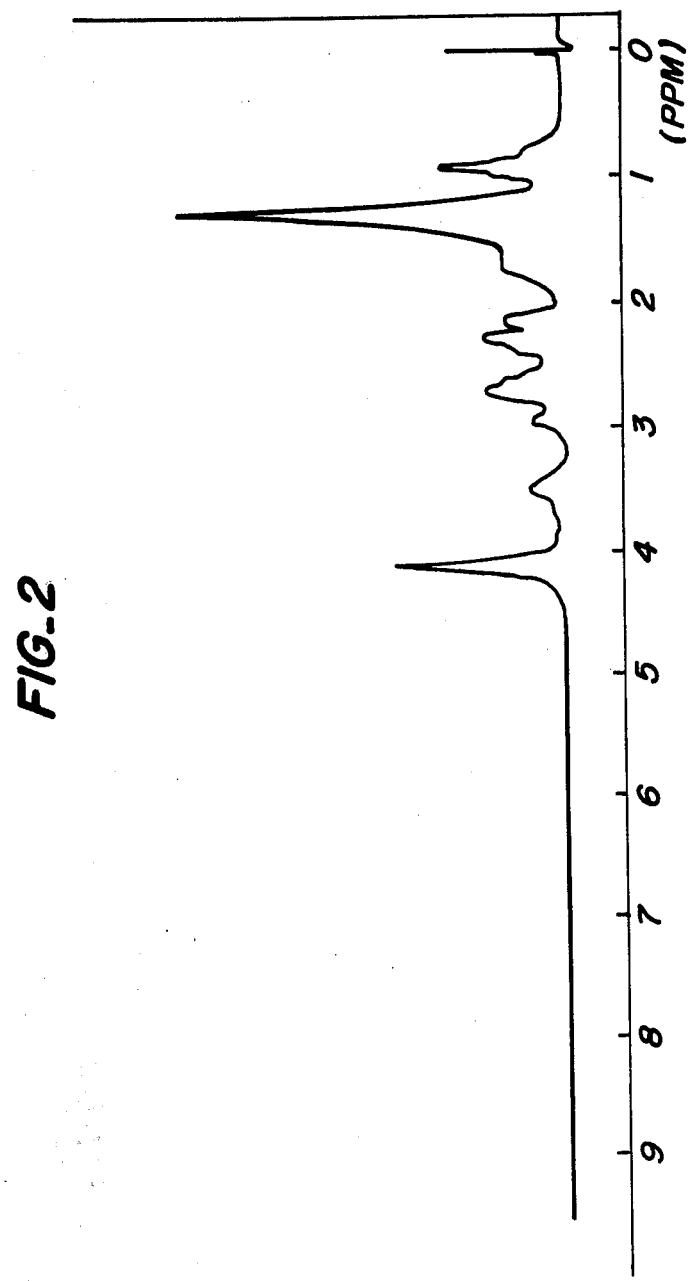
Figure 3:
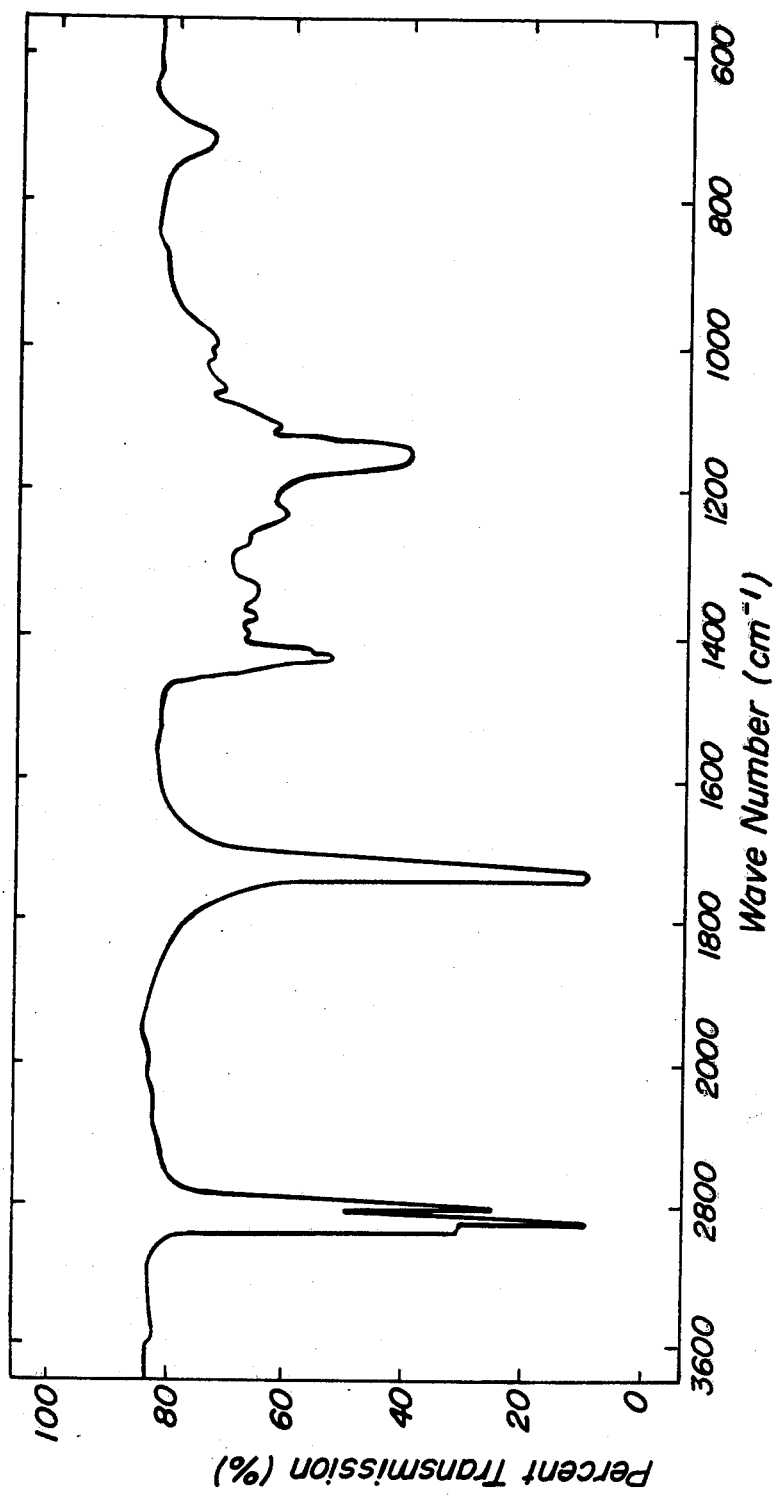
Figure 4:
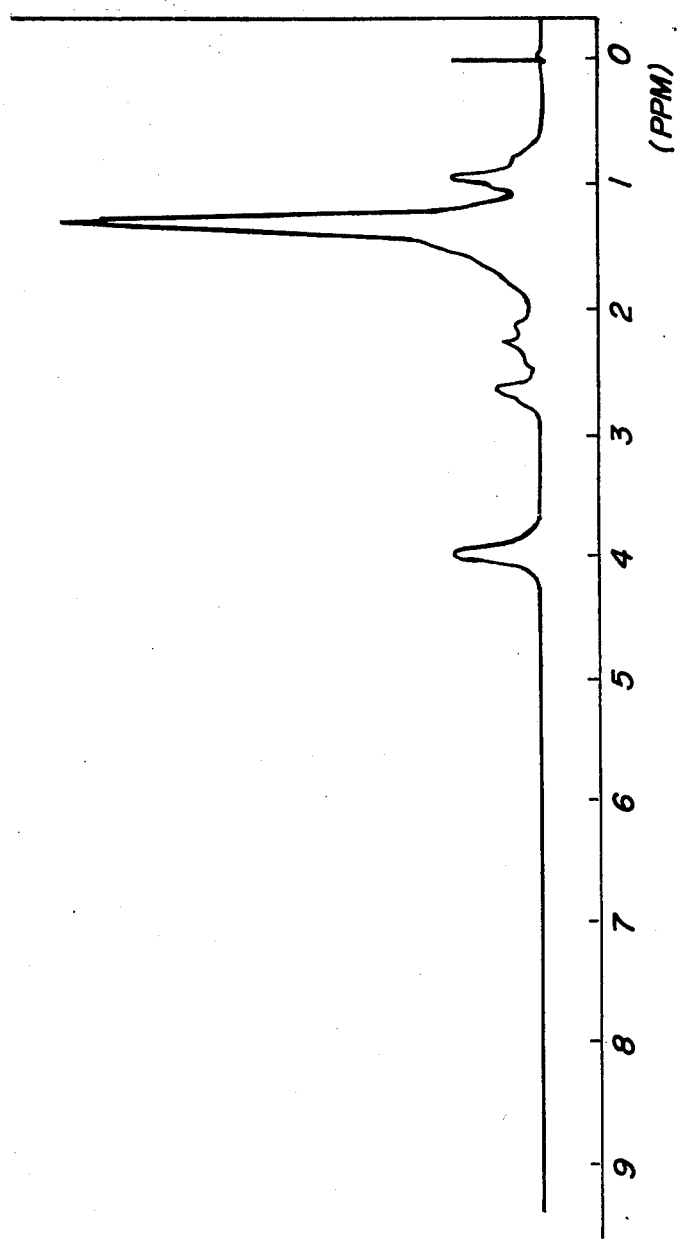

For a better understanding of the invention, reference is taken to the accompanying drawings, wherein FIG. 1 is a view of infrared absorption spectrum of the sulfur-containing complex ester obtained in Example 1, FIG. 2 is a view of nuclear magnetic resonance absorption spectrum of the same compound as in FIG. 1, FIG. 3 is a view of infrared absorption spectrum of the sulfur-containing complex ester obtained in Example 2 and FIG. 4 is a view of nuclear magnetic resonance absorption spectrum of the same compound as in FIG. 3.

The following examples are given for the purpose of illustration of this invention and are not intended as limitations thereof. In the examples, "%" means % by weight.

EXAMPLE 1

A mixture of 136 g (1 mole) of pentaerythritol, 89 g (0.5 mole) of thiodipropionic acid, 436 g (2.9 moles) of a monobasic acid mixture composed of 3% of caproic acid, 72% of caprylic acid and 25% of capric acid, 3.5 g of p-toluenesulfonic acid and 700 g of xylene was charged in a four-necked flask of 3l capacity provided with a reflux condenser equipped with a water separator, a stirrer, a thermometer and a nitrogen gas blowing pipe, and heated at 145°–155° C. for 10 hours under reflux of xylene while removing the distilled water. In this reaction, the acid value of the reaction mixture was decreased to 2.3. Then, the reaction mixture was cooled to 90° C. and stirred for 30 minutes together with a 0.5% aqueous solution of sodium hydroxide to neutarilize the free fatty acids and catalyst. After the aqueous layer was separated from the reaction mixture, the resulting mass was washed with hot water and subjected to a vacuum distillation under a reduced pressure of 1–2 mmHg to remove the xylene and then heated up to 200° C. to remove completely volatile matters. Then, the mass was cooled to 70° C. and treated with 3 g of active carbon to obtain a sulfur-containing complex ester (Compound A). The resulting complex ester had an acid value of 0.1, a saponification value of 364 and a mean molecular weight of 1,042 measured by the vapor pressure osmometry. The elementary analysis value of the ester was C: 62.76%, H: 9.84% and S: 2.44% (calculated value, C: 65.28%, H: 9.84% and S: 2.76%). Other analysis values of the ester are shown in the following Table 1.

The infrared absorption spectrum of the ester is shown in FIG. 1, and the nuclear magnetic resonance absorption spectrum thereof is shown in FIG. 2.

EXAMPLE 2

A mixture of 134 g (1 mole) of trimethylolpropane, 119 g (0.67 mole) of thiodipropionic acid, 439 g (1.60 moles) of hydrogenated tallow fatty acid having an acid value of 204.6, 3.3 g of p-toluenesulfonic acid and 700 g of xylene was reacted in the same manner as described in Example 1 to obtain a reaction mixture having an acid value of 2.8. The reaction mixture was purified in the same manner as described in Example 1 to obtain a sulfur-containing complex ester (Compound B). The ester had an acid value of 0.2, a saponification value of 238, a mean molecular weight of 1,796 measured by the vapor pressure osmometry, and an elementary analysis value of C: 70.58%, H: 10.89% and S: 3.02% (calculated value, C: 72.14%, H: 10.22% and S: 3.21%). Other analysis values of the ester are shown in Table 1.

The infrared absorption spectrum of the ester is shown in FIG. 3 and the nuclear magnetic resonance absorption spectrum thereof is shown in FIG. 4.

EXAMPLE 3

A mixture of 134 g (1 mole) of trimethylolpropane, 89 g (0.5 mole) of thiodipropionic acid, 380 g (1.9 moles) of lauric acid, 4 g of p-toluenesulfonic acid and 700 g of xylene was reacted and the reaction mixture was purified in the same manners as described in Example 1 to obtain a sulfur-containing complex ester (Compound C). The analysis values of the ester are shown in Table 1.

EXAMPLE 4

A mixture of 92 g (1 mole) of glycerine, 89 g (0.5 mole) of thiodipropionic acid, 274 g (1.9 moles) of caprylic acid, 5 g of sulfuric acid and 700 g of xylene was reacted and the reaction mixture was purified in the same manners as described in Example 1 to obtain a sulfur-containing complex ester (Compound D). The analysis values of the ester are shown in Table 1.

EXAMPLE 5

A sulfur-containing complex ester (Compound E) was produced in the same procedure as described in Example 1, except that 254 g (1 mole) of dipentaerythritol, 89 g (0.5 mole) of thiodipropionic acid, 649 g (4.5 moles) of caprylic acid, 5 g of methanesulfonic acid and 700 g of xylene were used. The analysis values of the ester are shwon in Table 1.

EXAMPLE 6

A sulfur-containing complex ester (Compound F) was produced in the same procedure as described in Example 1, except that 120 g (1 mole) of trimethylolethane, 89 g (0.5 mole) of thiodipropionic acid, 274 g (1.9 moles) of 2-ethylhexanoic acid, 5 g of ethanesulfonic acid and 700 g of xylene were used. The analysis values of the ester are shown in Table 1.

erythritol, azelaic acid and caprylic acid, and a complex ester (Compound H, mean molecular weight: 1,911) synthesized from trimethylolpropane, adipic acid and palmitic acid, and further three kinds of esters and a mineral oil.

In the thermal stability test, about 0.5 g of each sample was accurately weighed in a Petri dish having a diameter of 90 mm and heated at 220° C. for 3 hours in an oven. The evaporation loss was expressed by the percentage of the ratio of the decreased weight of the sample to the original weight thereof. Formation of tar, and color and gelation of the sample were judged by the naked eye. It can be seen from Table 2 that the samples containing the sulfur-containing complex ester of the present invention are excellent in the thermal stability.

Table 2

| | Sample | Evaporation loss (%) | Formation of tar | Color Before heating | Color After heating | Gelation |
|---|---|---|---|---|---|---|
| Oil of the present invention | Compound A | 22.1 | none | light yellow | light yellow | none |
| | Compound B | 18.6 | none | light yellow | light yellow | none |
| | Compound C | 8.2 | none | light yellow | light yellow | none |
| | Compound D | 27.9 | none | light yellow | light yellow | none |
| | Compound E | 26.6 | none | light yellow | light yellow | none |
| | Compound F | 25.7 | none | light yellow | light yellow | none |
| | Compound C 40% + Trimethylolpropane trilaurate 60% | 9.7 | none | light yellow | light yellow | none |
| | Compound C 80% + 2-Ethylhexyl stearate 20% | 14.9 | none | light yellow | light yellow | none |
| Comparative oil | Compound G | 59.3 | none | light yellow | light yellow | gelled |
| | Compound H | 48.4 | none | light yellow | light yellow | gelled |
| | Trimethylolpropane trilaurate | 58.8 | none | light yellow | brown | gelled |
| | Oleyl oleate | 56.2 | tar is formed | light yellow | dark brown | gelled |
| | 2-Ethylhexyl stearate | 98.6 | tar is formed | colorless | brown | gelled |
| | Spindle oil | 98.3 | tar is formed | light yellow | dark brown | gelled |

EXAMPLE 7

A thermal stability test was carried out with respect to the sulfur-containing complex esters of the present invention, mixtures of the sulfur-containing complex ester of the present invention and other ester, and comparative oils. Table 2 shows the results of the test.

As the comparative oils, use was made of two kinds of complex esters commonly used as a textile treating composition, that is, a complex ester (Compound G, mean molecular weight: 1,089) synthesized from penta-

EXAMPLE 8

Each sample oil used in Example 7 was deposited to a fiber, and the fiber-to-metal friction coefficient was measured by the Roeder method. Table 3 shows the results.

The measuring was carried out under the following condition.

| | | |
|---|---|---|
| Fiber | : | Polyester filament, 75 deniers. |
| Amount of oil deposited | : | 1.5% |
| Speed of filament | : | 300 m/min. |

Table 1

| Sylfur-containing Complex ester | Mean molecular weight | S content (%) Observed value | S content (%) Calculated value | Kinematic viscosity (est.) 100° F | Kinematic viscosity (est.) 210° F | Viscosity index $VI_E$ | Pour point (° C) |
|---|---|---|---|---|---|---|---|
| Compound A | 1042 | 2.44 | 2.76 | 209 | 21.4 | 132 | −28 |
| Compound B | 1796 | 3.02 | 3.21 | 473 | 45.1 | 158 | 30 |
| Compound C | 994 | 2.78 | 2.90 | 162 | 20.6 | 159 | −7.5 |
| Compound D | 727 | 3.83 | 3.97 | 69.3 | 10.1 | 142 | −37.5 |
| Compound E | 1610 | 1.58 | 1.79 | 349 | 35.1 | 155 | −12.5 |
| Compound F | 804 | 3.34 | 3.75 | 228 | 20.1 | 111 | −27.5 |

| | | |
|---|---|---|
| Metal | : | Iron |
| Relative humidity | : | 65% |
| Temperature | : | 20° C |

Table 3

| Sample | Friction coefficient |
|---|---|
| Compound A | 0.39 |
| Compound B | 0.40 |
| Compound C | 0.37 |

Table 3-continued

| | | |
|---|---|---|
| Oil of the present invention | Compound D | 0.35 |
| | Compound E | 0.39 |
| | Compound C 40% + Trimethylolpropane trilaurate 60% | 0.39 |
| | Compound C 80% + | 0.34 |

Table 4

| Ingredient | Spin finishing composition (%) | | | | | | | | | | | |
|---|---|---|---|---|---|---|---|---|---|---|---|---|
| | Present invention | | | | | | | | Comparison | | | |
| | No. 1 | No. 2 | No. 3 | No. 4 | No. 5 | No. 6 | No. 7 | No. 8 | No. 9 | No. 10 | No. 11 | No. 12 |
| Compound A | 70 | | | | | | | | | | | |
| Compound B | | 70 | | | | | | | | | | |
| Compound C | | | 70 | | | | 35 | 60 | | | | |
| Compound D | | | | 70 | | | | | | | | |
| Compound E | | | | | 70 | | | | | | | |
| Compound F | | | | | | 70 | | | | | | |
| Compound G | | | | | | | | | 70 | | | |
| Compound H | | | | | | | | | | 70 | | |
| Trimethylolpropane trilaurate | 20 | 20 | 20 | 20 | 20 | 20 | 20 | | 20 | 20 | 20 | 60 |
| 2-Ethylhexyl stearate | | | | | | | 35 | | | | 35 | |
| Spindle oil | | | | | | | | | | | 35 | |
| Polyoxyethylene (20 moles) castor oil | | | | | | | | 35 | | | | 35 |
| Polyoxyethylene (10 moles) lauryl ether | 4 | 4 | 4 | 4 | 4 | 4 | 4 | 5 | 4 | 4 | 4 | 5 |
| Polyoxyethylene (20 moles) oleate | 5 | 5 | 5 | 5 | 5 | 5 | 5 | | 5 | 5 | 5 | |
| Sodium lauryl phosphate | 1 | 1 | 1 | 1 | 1 | 1 | 1 | | 1 | 1 | 1 | |

| | | |
|---|---|---|
| Comparative oil | 2-Ethylhexyl stearate 20% Compound G | 0.38 |
| | Compound H | 0.37 |
| | Trimethylolpropane trilaurate | 0.41 |
| | Oleyl oleate | 0.32 |
| | 2-Ethylhexyl stearate | 0.34 |

It can be seen from Table 3 that the oils containing the sulfur-containing complex ester of the present invention have substantially the same effect for lowering the fiber-to-metal friction coefficient as that of the comparative oils, which are commonly used as lubricating oils, and have an excellent lubricity.

EXAMPLE 9

Each of the spin finishing compositions having a composition shown in the following Table 4 was formed into a 15% aqueous emulsion and deposited to a polyester filament yarn (75 deniers/24 filaments) in an amount of 1%, calculated as the spin finishing composition, based on the weight of the yarn. The yarn was hot drawn to 2 times its original length at a heater plate temperature of 200° C. in a conventional manner.

When the yarn was treated with a spin finishing compsotion of the present invention (Composition Nos. 1-8), there were substantially no smoke generation and formation of tar on the heater plate during the hot drawing, and the hot drawing step was able to be carried out very smoothly. While, when the yarn was treated with a commonly used spin finishing composition shown as a comparison (Composition Nos. 9-12), smoke generation and formation of tar occurred on the heater plate.

What is claimed is:

1. Sulfur-containing complex esters composed of thiodipropionic acid, polyhydric alcohols having at least three valencies and monobasic acids having 5-24 carbon atoms.

2. The sulfur-containing complex esters as claimed in claim 1, wherein the polyhydric alcohols are selected from the group consisting of trimethylolpropane, trimethylolethane, glycerine, pentaerythritol, and dipentaerythritol.

3. Spin finishing compositions consisting mainly of sulfur-containing complex esters composed of thiodipropionic acid, polyhydric alcohols having at least three valencies and monobasic acids having 5-24 carbon atoms, surface active agents and antistatic agents.

4. The spin finishing compositions as calimed in claim 3, wherein the polyhydric alcohols are selected from the group consisting of trimethylolpropane, trimethylolethane, glycerine, pentaerythritol, and dipentaerythritol.

5. The spin finishing compositions as claimed in claim 3, wherein the sulfur-containing complex esters are 50-98% by weight, the surface active agents are 1-45% by weight and the antistatic agents are 0-5% by weight.

* * * * *